US012175667B2

(12) United States Patent
Chitiboi et al.

(10) Patent No.: US 12,175,667 B2
(45) Date of Patent: Dec. 24, 2024

(54) ON-SITE TRAINING OF A MACHINE-LEARNING ALGORITHM FOR GENERATING SYNTHETIC IMAGING DATA

(71) Applicant: SIEMENS HEALTHINEERS AG, Forchheim (DE)

(72) Inventors: Teodora Marina Chitiboi, Hamburg (DE); Puneet Sharma, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 368 days.

(21) Appl. No.: 17/648,949

(22) Filed: Jan. 26, 2022

(65) Prior Publication Data

US 2022/0292673 A1  Sep. 15, 2022

(30) Foreign Application Priority Data

Mar. 12, 2021  (EP) .................................. 21162327

(51) Int. Cl.
*G06T 7/11* (2017.01)
*G06N 20/20* (2019.01)
*G06T 7/00* (2017.01)

(52) U.S. Cl.
CPC .......... *G06T 7/0012* (2013.01); *G06N 20/20* (2019.01); *G06T 7/11* (2017.01); *G06T 2207/20081* (2013.01); *G06T 2207/30168* (2013.01)

(58) Field of Classification Search
CPC ............... G06T 7/0012; G06T 7/11; G06T 2207/20081; G06T 2207/30168; G06N 20/20
See application file for complete search history.

(56) References Cited

U.S. PATENT DOCUMENTS

| 2017/0357844 | A1* | 12/2017 | Comaniciu | ............ G16H 30/00 |
| 2019/0046068 | A1 | 2/2019 | Ceccaldi et al. | |
| 2019/0139641 | A1 | 5/2019 | Itu et al. | |
| 2019/0148006 | A1* | 5/2019 | Ahmed | ............... A61B 5/0013 |
| | | | | 705/2 |
| 2019/0332900 | A1* | 10/2019 | Sjolund | ................... G06T 9/002 |
| 2020/0134446 | A1* | 4/2020 | Soni | ........................ G06N 3/047 |
| 2020/0286614 | A1* | 9/2020 | Do | ........................... G06N 7/01 |

FOREIGN PATENT DOCUMENTS

| EP | 3576020 A1 | 12/2019 |
| WO | 2019051359 A1 | 3/2019 |
| WO | 2019211307 A1 | 11/2019 |

OTHER PUBLICATIONS

Dwork C, Roth A. The algorithmic foundations of differential privacy. Foundations and Trends in TheoreticalComputer Science. Aug. 11, 2014;9(3-4):211-407.

(Continued)

*Primary Examiner* — Syed Haider

(57) ABSTRACT

Techniques of training an image-synthesis ML algorithm are disclosed. The image-synthesis ML algorithm can be used to generate synthetic imaging data. The synthetic imaging data can be used, in turn, to train a further ML algorithm. The further ML algorithm may be configured to perform image-processing tasks on the respective imaging data.

15 Claims, 5 Drawing Sheets

(56) References Cited

OTHER PUBLICATIONS

Ronneberger, Olaf, Philipp Fischer, and Thomas Brox. "U-net: Convolutional networks for biomedical image segmentation." In International Conference on Medical image computing and computer-assisted intervention, pp. 234-241. Springer, Cham, 2015.
Sahiner, Berkman, et al. "Deep learning in medical imaging and radiation therapy." Medical physics 46.1 (2019): e1-e36.
Taesung Park, Ming-Yu Liu, Ting-ChunWang, Jun-Yan Zhu. Semantic Image Synthesis with Spatially-Adaptive Normalization. 2019, CVPR.
Extended European Search Report (EESR) mailed Aug. 11, 2021 in corresponding European Patent Application No. 21162327.7.

\* cited by examiner

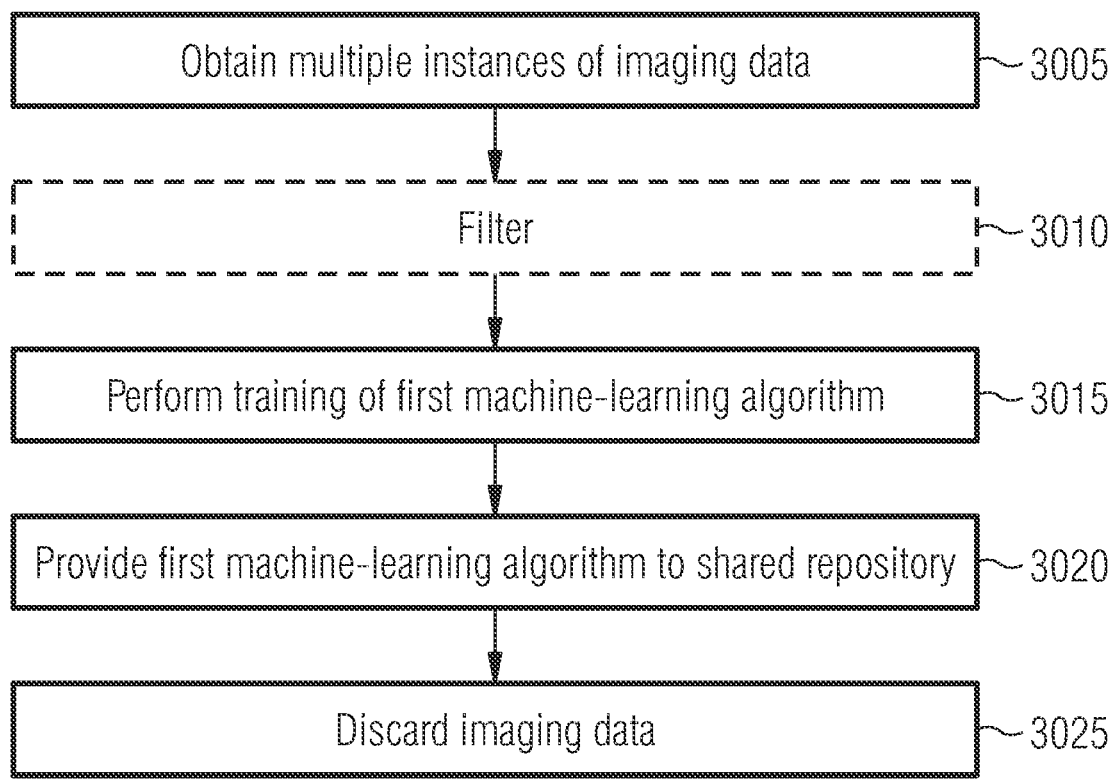

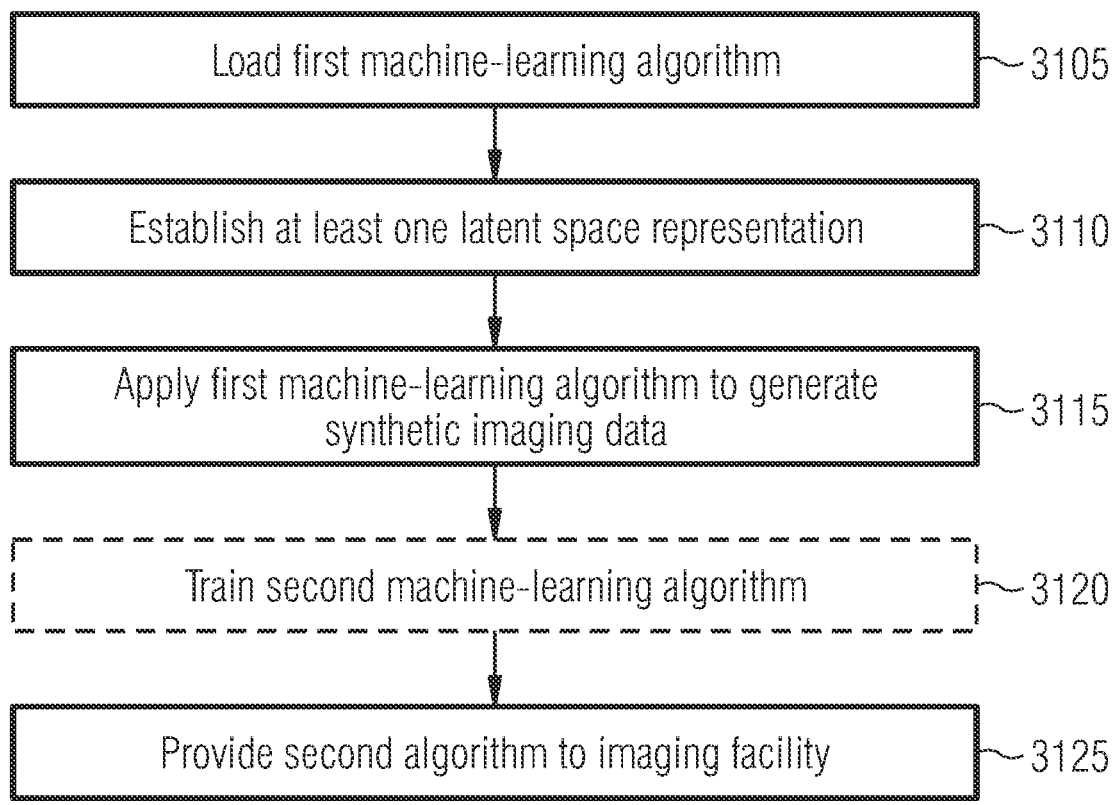

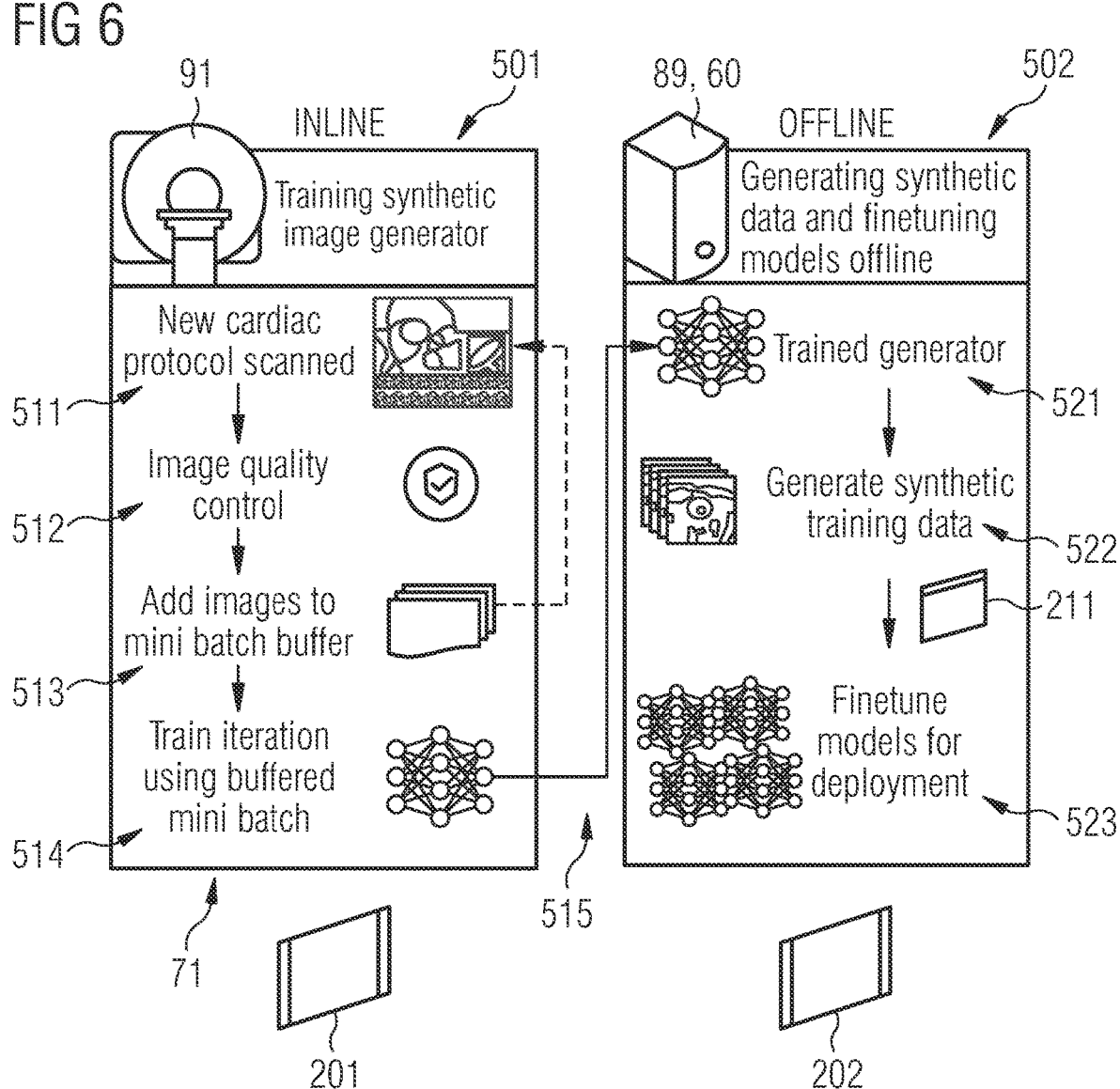

ON-SITE TRAINING OF A MACHINE-LEARNING ALGORITHM FOR GENERATING SYNTHETIC IMAGING DATA

RELATED APPLICATION

This application claims the benefit of 21162327.7, filed Mar. 12, 2021, which is hereby incorporated by reference in its entirety.

TECHNICAL FIELD

Various examples of the disclosure relate to facilitating a training of a machine-learning algorithm configured to process medical imaging data. Various examples of the disclosure specifically relate to training of a further machine-learning algorithm, the further machine-learning algorithm being configured to provide synthetic training imaging data for training the machine-learning algorithm.

BACKGROUND

There are various use cases in the medical field where machine-learning algorithms—e.g., deep neural networks or support vector machines—are applied. Examples include segmentation and detection of anomalies, or classification.

It has been observed that obtaining sufficient training data to train a machine-learning (ML) algorithm to perform the respective task at a required accuracy can be challenging. This is specifically true for an ML algorithm that processes medical imaging data. Oftentimes, suitable medical imaging data is only available to a limited degree.

SUMMARY

Accordingly, there is a need for advanced techniques of facilitating training of an ML algorithm. Specifically, there is a need for advanced techniques of facilitating training of the ML algorithm that processes medical imaging data.

Hereinafter, techniques of training an image-synthesis ML algorithm will be described. The image-synthesis ML algorithm can be used to generate synthetic imaging data. The synthetic imaging data can be used, in turn, to train a further ML algorithm. The further ML algorithm may be configured to perform image-processing tasks on the respective imaging data.

A computer-implemented method of performing a first training of a first ML algorithm is provided. The first ML algorithm is for generating synthetic imaging data of an anatomical target region of at least one patient. The method includes obtaining multiple instances of imaging data of the anatomical target region of the at least one patient. The multiple instances of the imaging data are acquired at an imaging facility. The method also includes, on-site at the imaging facility and based on the multiple instances of the imaging data, performing the first training of the first ML algorithm for generating the synthetic imaging data. The method also includes, upon completion of the first training: providing at least parameter values of the first ML algorithm to a shared repository. Thereby, a second training of a second ML algorithm is enabled based on further synthetic imaging data that is generated by the first ML algorithm using the parameter values.

A computer program, a computer-program product, or a non-transitory computer-readable storage medium includes program code. The program code can be loaded and executed by at least one processor. Upon loading and executing the program code, the at least one processor performs a method of performing a first training of a first ML algorithm. The first ML algorithm is for generating synthetic imaging data of an anatomical target region of at least one patient. The method includes obtaining multiple instances of imaging data of the anatomical target region of the at least one patient. The multiple instances of the imaging data are acquired at an imaging facility. The method also includes, on-site at the imaging facility and based on the multiple instances of the imaging data, performing the first training of the first ML algorithm for generating the synthetic imaging data. The method also includes, upon completion of the first training: providing at least parameter values of the first ML algorithm to a shared repository. Thereby, a second training of a second ML algorithm is enabled based on further synthetic imaging data that is generated by the first ML algorithm using the parameter values.

A device includes a processor and a memory. The processor is configured to load program code from the memory and execute the program code. Upon executing the program code, the processor performs a method of performing a first training of a first ML algorithm. The first ML algorithm is for generating synthetic imaging data of an anatomical target region of at least one patient. The method includes obtaining multiple instances of imaging data of the anatomical target region of the at least one patient. The multiple instances of the imaging data are acquired at an imaging facility. The method also includes, on-site at the imaging facility and based on the multiple instances of the imaging data, performing the first training of the first ML algorithm for generating the synthetic imaging data. The method also includes, upon completion of the first training: providing at least parameter values of the first ML algorithm to a shared repository. Thereby, a second training of a second ML algorithm is enabled based on further synthetic imaging data that is generated by the first ML algorithm using the parameter values.

A computer-implemented method for generating synthetic imaging data of an anatomical target region includes establishing at least one latent space representation associated with the anatomical target region of at least one patient. The method also includes applying a trained first ML algorithm to the at least one latent space representation and generating, by the trained first ML algorithm, the synthetic imaging data to enable a second training of a second ML algorithm based on the synthetic imaging data.

A computer program, a computer-program product, or a non-transitory computer-readable storage medium includes program code. The program code can be loaded and executed by at least one processor. Upon loading and executing the program code, the at least one processor performs a method for generating synthetic imaging data of an anatomical target region. The method includes establishing at least one latent space representation associated with the anatomical target region of at least one patient. The method also includes applying a trained first ML algorithm to the at least one latent space representation and generating, by the trained first ML algorithm, the synthetic imaging data to enable a second training of a second ML algorithm based on the synthetic imaging data.

A device includes a processor and a memory. The processor is configured to load program code from the memory and execute the program code. Upon executing the program code, the processor performs a method for generating synthetic imaging data of an anatomical target region. The method includes establishing at least one latent space representation associated with the anatomical target region of at least one patient. The method also includes applying a trained first ML algorithm to the at least one latent space representation and generating, by the trained first ML algorithm, the synthetic imaging data to enable a second training of a second ML algorithm based on the synthetic imaging data.

It is to be understood that the features mentioned above and those yet to be explained below may be used not only in the respective combinations indicated, but also in other combinations or in isolation without departing from the scope of the invention.

BRIEF DESCRIPTION OF THE DRAWINGS

FIG. 4 is a flowchart of a method according to various examples.

FIG. 5 is a flowchart of a method according to various examples.

FIG. 6 schematically illustrates a workflow according to various examples.

DETAILED DESCRIPTION OF THE DRAWINGS

Figure 1:
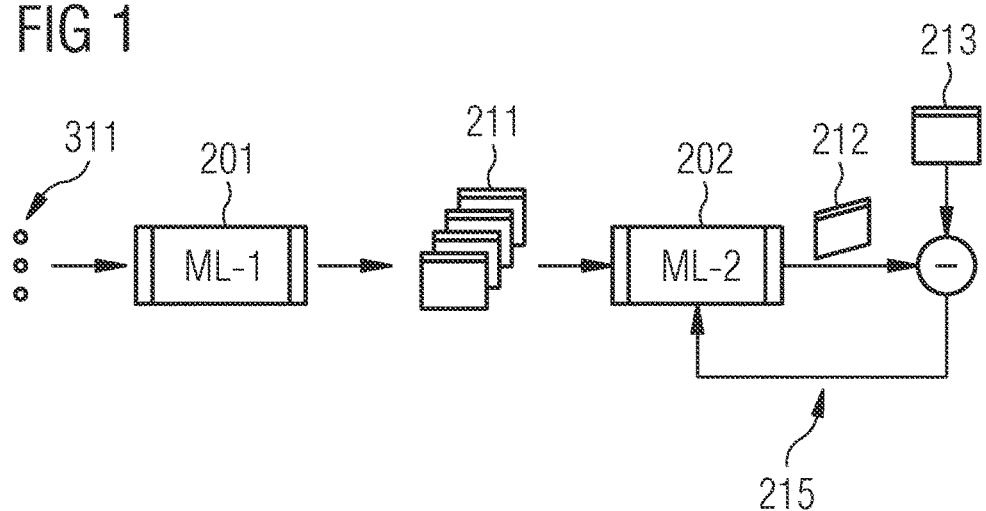
FIG. 1 schematically illustrates one embodiment of a first ML algorithm and a second ML algorithm, the first ML algorithm providing synthetic imaging data for training the second ML algorithm according to various examples (image-synthesis ML algorithm).

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various techniques disclosed herein generally relate to facilitating training of an ML algorithm. The ML algorithm can be configured to process imaging data. For example, the ML algorithm could be configured to process medical imaging data, e.g., depicting an anatomical target region of a patient, e.g., the heart, the liver, the brain, etc. In other examples, other kind of imaging data could be processed, e.g., projection imaging data, e.g., for security scanners or material inspection.

According to the disclosure, various kinds and types of imaging data may be processed. As a general rule, it would be possible that the ML algorithm processes 2-D images or raw data obtained in K-space. The ML algorithm may process 3-D depth data, e.g., point clouds or depth maps. The ML algorithm may process time varying data, where one dimension stores an image or volume representation at different points in time.

Hereinafter, various examples will be described in the context of an ML algorithm configured for processing medical imaging data. However, similar techniques can be readily applied to other kinds and types of semantic context of the imaging data. For sake of simplicity, the ML algorithm will be referred to as medical-imaging ML algorithm, hereinafter.

As a general rule, various kinds and types of medical imaging data can be subject to the techniques described herein. To give a few examples, it would be possible to use magnetic resonance imaging (MRI) imaging data, e.g., raw data in K-space or pre-reconstructed images. Another example would pertain to computed tomography (CT) imaging data, e.g., projection views or pre-reconstructed images. Yet another example would pertain to Positron Emission Tomography (PET) imaging data. Other examples include ultrasound images.

As a general rule, various kinds and types of medical-imaging ML algorithms can benefit from the techniques described herein. For instance, it would be possible to use a deep neural network, e.g., a convolutional neural network having one or more convolutional layers performing convolutions between the input data and a kernel. It would also be possible to use a support vector machine, to give just a few examples. A U-net architecture may be used, see, e.g., Ronneberger, O., Fischer, P. and Brox, T., 2015, October. U-net: Convolutional networks for biomedical image segmentation. In *International Conference on Medical image computing and computer-assisted intervention* (pp. 234-241). Springer, Cham.

In the examples described herein, the medical-imaging ML algorithm can be configured to perform various tasks when processing the medical imaging data. For instance, the medical-imaging ML algorithm could be configured to perform a segmentation of medical imaging data. For instance, it would be possible to segment predefined anatomical features. In a further example, the medical-imaging ML algorithm could be configured to perform an object detection. For instance, a bounding box could be drawn around a predefined object that is detected in the medical image data. Predefined objects could be predefined anatomical features, e.g., certain organs or vessels, a tumor site, etc. It would also be possible to detect anomalies. Yet a further task would be filtering or denoising. For instance, it would be possible to remove artifacts from the imaging modality, e.g., blurs or flare spots. Background noise could be suppressed or removed. Yet a further task would be up-sampling, to thereby increase a resolution of the medical imaging data. Yet a further task of the medical-imaging ML algorithm could be image reconstruction. For instance, for magnetic resonance imaging data, the raw imaging data is available in K-space. Sometimes, the K-space is undersampled (e.g., with respect to a certain field-of-view, considering Nyquist's theorem), i.e., a direct Fourier transform would result in aliasing artifacts. In such scenarios, image reconstruction can be implemented using an appropriate medical-imaging ML algorithm. For example, techniques are known where an unrolled neural network is used; here, a regularization operation can be implemented using the medical-imaging ML algorithm. As will be appreciated from the above, the particular type of the medical-imaging ML algorithm is not germane for the functioning of the techniques described herein. Rather, various kinds and types of medical-imaging ML algorithms can benefit from the techniques described herein, i.e., can be accurately trained.

Various techniques are based on the finding that well-adapted training imaging data may be required to accurately train a medical-imaging ML algorithm. For instance, it has been observed that the amount of training imaging data and the variability of the training imaging data can correlate with an accuracy of the medical-imaging ML algorithm; i.e., the more training imaging data having sufficient variability (to capture domain-specific features) is available, the more accurate the training of the medical-imaging machine learning algorithm. Secondly, it has been observed that domain-specific training imaging data can be helpful to obtain an accurate training state of the medical-imaging ML algorithm. For instance, depending on the particular imaging facility or the observed target, the imaging data input to the medical-imaging ML algorithm can vary. Then, domain-specific training—i.e., training specific to the observed target and/or the specific imaging facility—can be required to achieve a higher accuracy. To give an example, it has been observed that even after a medical-imaging ML algorithm has been trained on a large data set of training imaging data that is generic, i.e., unspecific to a specific domain, further fine-tuning of the training can be required to adapt the medical-imaging ML algorithm to a particular patient population (e.g., adult to children), imaging modality (e.g., 1.5 Tesla MRI scanner versus 3 Tesla MRI scanner, different undersampling acceleration factors, etc. to give just a few examples). I.e., re-training or fine-tuning with domain specific training imaging data can be helpful. Obtaining respective domain-specific training imaging data can be challenging according to reference techniques.

According to various examples, it is possible to facilitate such training, in particular, domain-specific training. Tailored training imaging data can be provided; i.e., domain-specific training imaging data can be provided.

Various techniques are based on the finding that a further ML algorithm—hereinafter referred to as image-synthesis ML algorithm—can be used to generate/infer synthetic training imaging data of an anatomical target region. The synthetic training imaging data can then be used to enable the training of the medical-imaging ML algorithm.

The general concept of synthetic image generation with ML algorithms has been shown to produce realistic results, including for medical imaging. Synthetic image generation can typically help when data is scarce to improve the accuracy of a machine learning model.

For example, a generative adversarial network architecture can be used to implement the image-synthesis ML algorithm. More generally, different approaches exist in the literature for synthetic data generation. E.g., GauGan approach where a neural network learns to produce images given their segmentation as input; see Park, Taesung, et al. "Semantic image synthesis with spatially-adaptive normalization." *Proceedings of the IEEE/CVF Conference on Computer Vision and Pattern Recognition.* 2019.

For example, the image-synthesis ML algorithm can include a decoder that decodes at least one latent space representation—i.e., a particular sample of the latent space defined by associated imaging data,—to thereby obtain synthetic imaging data. Feature expansion can be performed.

According to various examples, it is possible to perform a training of the image-synthesis ML algorithm. The training is based on multiple instances of imaging data of the anatomical target region for which the image-synthesis ML algorithm generates the synthetic training imaging data. The training imaging data can be acquired at an imaging facility.

During inference, it is possible to sample the latent space. I.e., multiple latent space representations—i.e., different feature vectors sampling the latent space—can be used to determine synthetic imaging data.

As a general rule, the image-synthesis ML algorithm may take, as an input, a segmentation map representing the anatomical target region present in the imaging data. Then, synthetic imaging data can be provided for a respectively shaped anatomical target region.

It would also be possible to randomly sample the latent space, e.g., determine multiple latent space representations and provide these as an input to the image-synthesis algorithm. An example of the latent space representation can include a feature vector containing a set of numerical values representing image features corresponding to anatomical characteristics associated with the anatomical target region of the at least one patient. Other examples are possible, e.g., image appearance, presence of a pathology, anatomy properties, etc.

The image-synthesis ML algorithm can be trained as a variational autoencoder to learn the statistical distribution of the training image data. When performing the training of the image-synthesis ML algorithm, the image-synthesis ML algorithm learns how to reproduce a real image by first encoding it into a latent space representation—i.e., a latent vector z using the encoder network—and then expanding the latent vector z into an image similar to the input image using a decoder network which implements the image-synthesis ML algorithm. Based on the distribution of the training imaging data (e.g., by considering multiple instances of the training imaging data), various latent space representations distributed across the latent space can be determined.

During the training of the image-synthesis ML algorithm, it is possible to update the parameter values of the image-synthesis ML algorithm based on a comparison between the imaging data and the corresponding generated imaging data. This comparison can be implemented as a loss function. An iterative numerical optimization can be used to update the parameter values. Backpropagation can be used. I.e., it can be judged how well the image-synthesis ML algorithm is able to reconstruct the original imaging data based on the latent space representation; and this reconstruction can be optimized.

The image-synthesis ML algorithm thus learns a latent space representation of the multiple instances of the imaging data that it was trained on, but it does not learn individual images of the imaging data pixel-by-pixel. Therefore, the synthetic images are never identical to real patient data and they cannot be traced back to a specific patient.

Then, to generate synthetic training imaging data for the medical-imaging ML algorithm, the decoder network acts like a synthetic image generator. During inference of the image-synthesis ML algorithm, corresponding to the training of the medical-imaging ML algorithm, the latent space(s) of the trained image-synthesis ML algorithm can be randomly sampled to produce the synthetic training imaging data. In other words, multiple possible latent space representations associated with the anatomical target region can be sampled.

More specifically, it would be possible to establish—e.g., by random sampling and/or by user input and/or based on some reference imaging data and/or based on an instance vector z of latent space representation and/or based on a segmentation of the anatomical target region—at least one latent space representation associated with the anatomical target region of the patient. Thereby, the trained image-synthesis ML algorithm can generate the synthetic medical imaging data that enables the training of the medical-imaging ML algorithm (synthetic training medical imaging data).

Upon completion of the training of the medical-imaging ML algorithm, the medical-imaging ML algorithm can be provided to an imaging facility. At the imaging facility, the trained medical-imaging ML algorithm can the support medical personnel in the analysis or processing of medical imaging data.

According to the techniques described herein, it is possible that the training of the image-synthesis ML algorithm is performed on-site at the imaging facility that is used to acquire the multiple instances of the imaging data of the anatomical target region. Here, "on-site" can mean that a respective processing device that performs the training of the image-synthesis ML algorithm is located in the same local area network or virtual private area network as the imaging facility. "On-site" can mean that the respective processing device is located at the same premise as the imaging facility, e.g., at the same hospital or radiography center. "On-site" can mean that the training is performed before the training imaging data is exported and sent to a picture archiving and communication system (PACS). "On-site" can even mean that the processor performing the training is an integrated processor of the imaging facility, e.g., also providing control of the imaging routine.

Once the image-synthesis ML algorithm has been trained, it is then possible to provide at least parameter values of the image-synthesis ML algorithm to a shared repository. For instance, the weights of a convolutional neural network model implementing the image-synthesis ML algorithm that are set by the training can be provided to the shared repository. It would also be possible to provide the entire image-synthesis ML algorithm to the shared repository.

The shared repository can be located off-site with respect to the imaging facility. I.e., it would be possible that the shared repository is not located in the same local area network or virtual private area network is the imaging facility. For instance, the shared repository could be located in a data cloud. The shared repository could be at a server farm. Off-premises storage would be possible. Specifically, a data connection between the processing device that performs the training of the image-synthesis ML algorithm and the shared repository may have a limited bandwidth. For example, this data connection could be implemented via the Internet.

By such techniques, it is possible to limit the amount of data that is provided to the shared repository. Specifically, it would be possible to not provide the training imaging data to the shared repository. The training imaging data implements payload data, i.e., data of high volume that is used to perform the training. By providing, to the shared repository, the image-synthesis ML algorithm or at least parameter values thereof, the amount of data can be significantly reduced. The privacy of the training imaging data may not be mitigated. Rather than providing the training imaging data itself, it is possible to provide, to the shared repository, inferred information in the form of the parameter values of the image-synthesis ML algorithm itself. Thus, it is not required to reveal the identity or characteristics of individual imaging data used for the training of the image-synthesis ML algorithm. For example, the imaging data used to train the image-synthesis ML algorithm never has to leave the hospital or imaging facility. Only the model weights leave the hospital, the imaging data used for the training could be discarded. It would be possible to only retain/store the at least one latent space representation thereof.

By using such techniques, medical-imaging ML algorithms can be (re-)trained to the specific patient distribution and image appearance of the respective imaging facilitate before deployment. Domain-specific training is possible. The algorithms are personalized to the needs of the specific radiology site.

No additional effort spent on collecting diverse data from different sites for algorithm optimization is required. There is no additional effort to retrospectively collect and curate data to for the purpose of finetuning the ML model.

FIG. 1 schematically illustrates aspects with respect to training a medical-imaging ML algorithm 202. The medical-imaging ML algorithm 202 is trained based on synthetic training imaging data 211. For example, based on the synthetic training imaging data 211, it would be possible to determine an output 212 with a ground truth 213; the ground truth 213 could be determined based on manual labeling or semi-automated labeling. A respective loss function can be defined, and a loss value can be determined by such comparison. Then, based on a respective loss value feedback 215, one or more parameter values of the medical-imaging ML algorithm 202 can be adjusted. For example, a gradient descent optimization technique may be used. Back propagation may be employed.

Various techniques described herein are concerned with determining the synthetic training imaging data 211. Specifically, the synthetic training imaging data 211 can be generated by an image-synthesis ML algorithm 201. The image-synthesis ML algorithm can be applied to one or more vector instances of a latent space, i.e., latent space representations 311 of an anatomical target region of a patient. Each time the image-synthesis ML algorithm 201 is applied to a given latent space representation 311, a respective instance of synthetic training medical imaging data is generated.

For instance, a given latent space representation 311 of the anatomical target region may include a feature vector containing a set of numerical values representing a set of image features corresponding to different characteristics of the respective anatomical target region, e.g., defining the circumference of the heart or a certain vessel, etc. It would alternatively or additionally be possible to specify other parameters of the anatomical target region using the one or more latent features of a latent space representation (values in the vector instance of the latent space), e.g., size, pathology, etc.

As a general rule, the latent space representation 311 could be indicative of a configuration of the imaging facility used to acquire a respective imaging data. The configuration could pertain, e.g., to a used protocol, e.g., MRI sequence, parameter settings of the imaging modality, etc.

It would be possible to randomly sample the latent space, e.g., determine the at least one latent space representation using randomization.

Then, the image-synthesis ML algorithm 201 can be applied to the at least one latent space representation 311 to generate the synthetic training medical imaging data 211 to enable the training of the medical-imaging ML algorithm 202. In the illustrated example of FIG. 1, multiple instances of the synthetic training medical imaging data generated, e.g., by using different feature vector instances from the latent space and input images to the image-synthesis ML algorithm 201.

Figure 2:
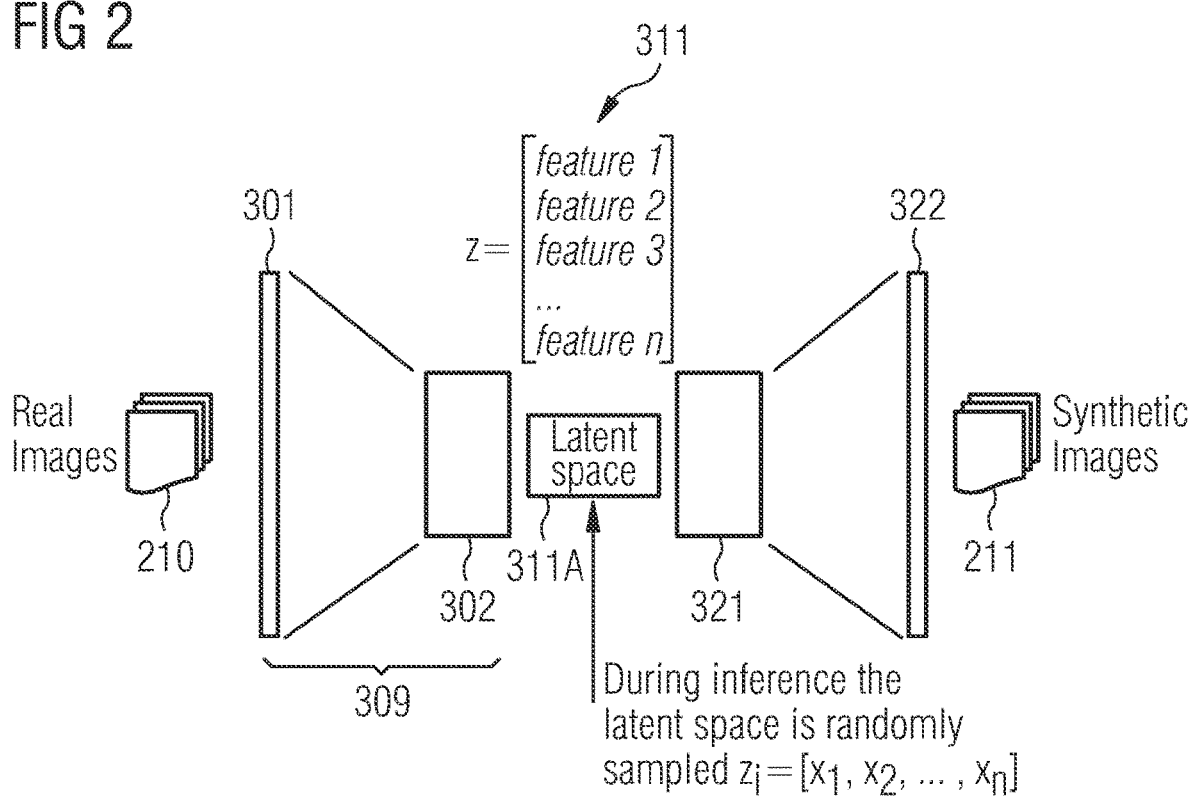
FIG. 2 schematically illustrates details with respect to an image-synthesis ML algorithm according to one embodiment.

FIG. 2 schematically illustrates aspects with respect to the image-synthesis ML algorithm 201. In the illustrated example, the image-synthesis ML algorithm 201 includes a decoder network to decode the latent space representations 311 to generate the synthetic medical imaging data 211. I.e., a feature vector serving as the input 321 can be expanded to provide, e.g., a 2D image as the output 322. The dimensionality is increased.

To learn the latent space representation 311 of the real data distribution, a further algorithm 309 may be used during training. During inference, the further algorithm 309 may not be required, anymore (during inference, the latent space 311A can be randomly sampled or the latent space representations 311 used for inference can be otherwise determined). The further algorithm 309 could be an image encoder network that learns the latent space representations 311 of the real images serving as the input 301. For instance, imaging data 210 acquired at an imaging facility—e.g., an MRI image, a CT image, etc.—may be provided as the input 301 of the algorithm 309 and the output 302 of the algorithm 309 may then be the latent space representation 311 of an anatomical target region included in the imaging data 210.

Figure 3:
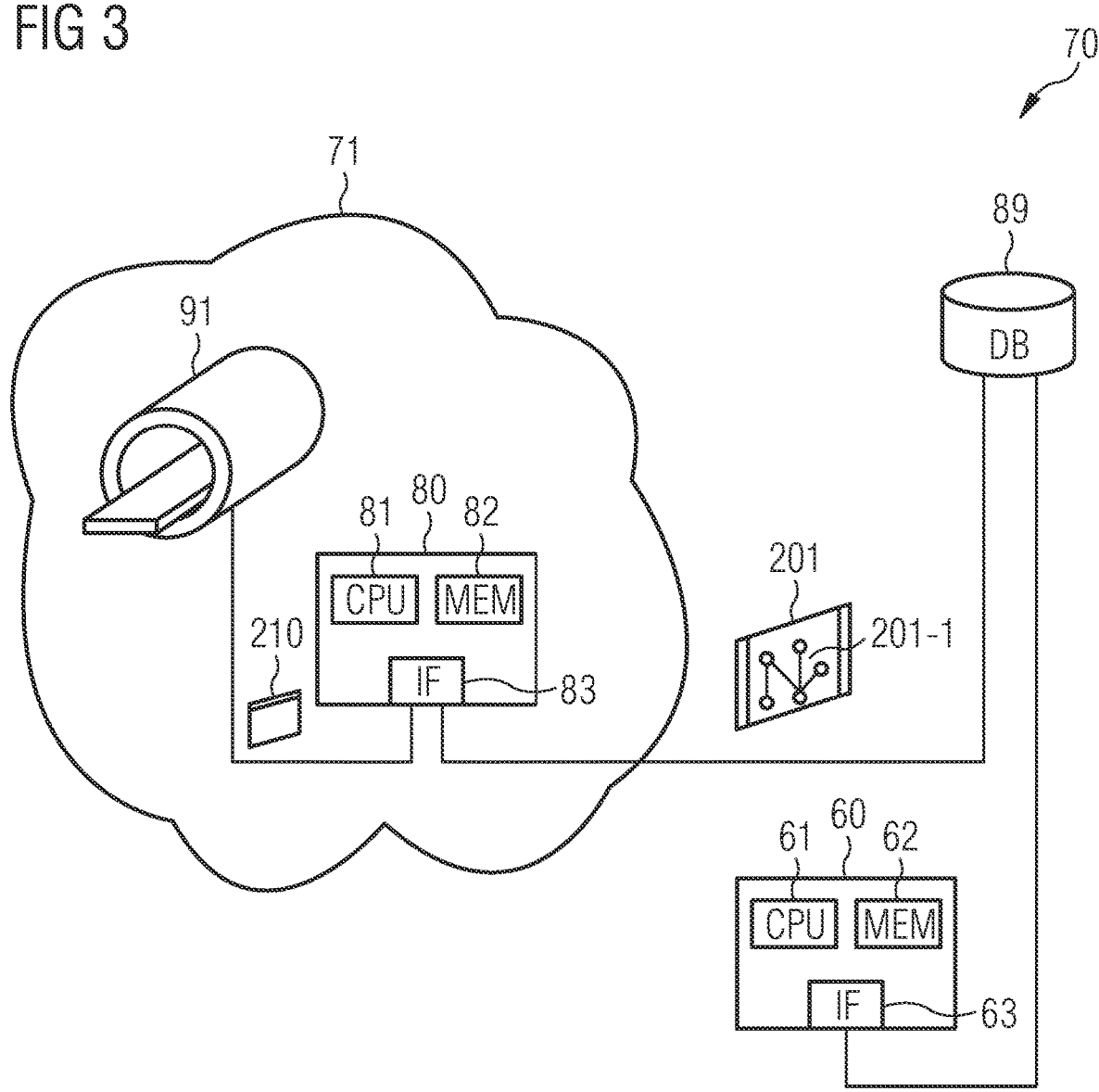
FIG. 3 is a schematic illustration of a system according to various examples.

FIG. 3 schematically illustrates a system 70 according to various examples. The system 70 includes an imaging facility 91, e.g., an MRI scanner or a CT scanner to give just two examples. The imaging facility 91 may be located at the hospital.

The system 70 also includes a device (computer) 80. The device 80 is located on-site at the imaging facility 91. For example, in the illustrated scenario, the device 80 and the imaging facility 90 one or both part of the same local area network 71. The device 80 includes a processor 81 and the memory 82. The device 80 also includes an interface 83. For instance, the processor 81 may receive medical imaging data 210 from the imaging facility 91 via the interface 83. The processor 81 may load program code from the memory 82 and execute the program code. Upon loading and executing the program code, the processor 81 may perform techniques as described herein, e.g., training a first ML algorithm based on imaging data from the imaging facility 91, filtering the imaging data prior to training the first ML algorithm, etc.

The processor 81, upon completing the training of the first machine learning algorithm 201, can then provide the first machine learning algorithm 201—or, at least, parameter values 201-1 (the parameter values 201-1 being set during the training) thereof—to the shared repository 89. This facilitates training of the second machine-learning algorithm 202 at a further device 60. Therefore, the first ML algorithm can be labeled image-synthesis ML algorithm.

The further device (computer) 60 is located off-premises with respect to the imaging facility 91, i.e., outside the local area network 71. The further device 60 includes a processor 61, a memory 62, and an interface 63. The processor 61 can load the parameter values 201-1 or the entire training machine ML algorithm 201 from the shared repository 89, and then generate synthetic medical imaging data using the image-synthesis ML algorithm 201 that is appropriately configured in accordance with the parameter values 201-1 (cf. synthetic training medical imaging data 211 in FIG. 1). The synthetic imaging data can then be used to train a second machine learning algorithm. The processor 61 can load and execute respective program code from the memory 62.

FIG. 4 is a flowchart of a method according to various examples. The method of FIG. 4 pertains to training of a first ML algorithm for generating synthetic imaging data of an anatomical target region.

The synthetic imaging data can be generated for the anatomical target region of at least one patient. The synthetic imaging data can depict the anatomical target region as if acquired using a certain imaging facility with a certain imaging protocol.

Once the first ML algorithm has been trained, the first ML algorithm can be used to generate further synthetic imaging data—i.e., synthetic training imaging data—and a further, second ML algorithm can be trained based on the synthetic training imaging data. I.e., the training phase of the second ML algorithm pertains to the inference phase of the first ML algorithm. Accordingly, the first ML algorithm can also be referred to as image-synthesis ML algorithm.

The method of FIG. 4 can be executed by at least one processor upon loading program code. For instance, the method of FIG. 4 could be executed by the processor 81 of the device 80, upon loading program code from the memory 82.

Optional boxes are labeled with dashed lines.

At box 3005, multiple instances of imaging data are obtained. Box 3005 could include acquisition of the multiple instances of the imaging data. Box 3005 could include sending control instructions to an imaging facility to acquire the multiple instances of the imaging data. Box 3005 could include loading the multiple instances of the imaging data from a buffer memory. For instance, during use of an imaging facility—e.g., an MRI or CT scan—it would be possible to buffer acquired images in a so-called mini-batch. Once the mini batch is full, the multiple instances of the imaging data can be obtained from the respective buffer memory.

The multiple instances of the imaging data could be acquired for multiple patients. Then, inter-patient variability can be considered when training the first ML algorithm. The multiple instances of the imaging data could be acquired using multiple configurations of the imaging facility. For instance, different parameters for the acquisition of images, e.g., exposure time, MRI scanning protocol, CT contrast, etc. could be selected. It would be possible that respective configuration data that is indicative of the respective configuration of the imaging facility for a given instance of the imaging data is also obtained at box 3005. As a general rule, a latent space representation of the medical imaging data can be indicative of the configuration.

At optional box 3010, the multiple instances of the imaging data are filtered, e.g., to implement a quality check. For example, the filtering can be based on the quality. Various quality metrics are possible, e.g., sharpness, contrast, motion blur, to give just a few examples. It would be possible to check whether the correct anatomy and/or view are present in the respective imaging data. It could be checked whether the imaging data depicts a calibration phantom (in which case it may be helpful to discard the respective instance of the imaging data).

Various examples to determine the quality are possible. For example, a further ML algorithm could be used to determine a score for the quality which scored can then be compared with the predefined threshold. Then, imaging data that has a quality greater than a predefined threshold can be retained; other imaging data can be discarded.

At box 3015, a training of the first ML algorithm is performed. This can include learning the latent space for each one of the anatomical regions, imaging protocols, or configurations. I.e., for each latent space, multiple latent space representations in the respective latent space could be determined, e.g., based on multiple instances of respective image data. An encoder network may be used for this purpose. Then, for a given latent space, the latent space representations in that latent space of the multiple instances of the image data can be processed by the decoder network implementing the first ML algorithm, to thereby obtain the synthetic imaging data. Then, a comparison can be made between the respective input, i.e., a given instance of the multiple instances of the imaging data, and an output, i.e., the synthetic imaging data, of the first ML algorithm. A loss function can be defined based on this comparison, and based on the value of the loss function, parameter values of the first ML algorithm can be updated.

The described combination of encoder network and auto-encoder network corresponds to a variational auto-encoder architecture.

Respective aspects with respect to the latent space representations and the operation of the first ML algorithm have been explained above in connection with FIG. 2 and the image-synthesis ML algorithm 201.

As a general rule, it would be possible that the first ML algorithm is in a pre-trained state when executing box 3015. For instance, the first ML algorithm may be pre-trained based on offline imaging data associated with the anatomical target region of further patients. Thereby, the training of box 3015 can add domain-specific training to the general training state.

Once the training of the first ML algorithm has been completed at box 3015, the first ML algorithm can be provided to a shared repository (cf. FIG. 3: shared repository 89). More generally, at least the parameter values of the first ML algorithm can be provided to the shared repository, at box 3020.

It would then be possible to discard the multiple instances of the imaging data used for the training of the image synthesis ML network, at optional box 3025. It would be possible to not provide the multiple instances of the imaging data used for the training to the shared repository.

Optionally, the latent space representations of the multiple instances of the imaging data could be stored, e.g., at the shared repository. The latent space representation could then be used as seed values for determining further latent space representations for which synthetic training medical imaging data could be determined. For example, an encoder network used during the training at box 3015 to determine the latent space representations of the imaging data may not be provided to the shared repository.

Once the parameter values of the first ML algorithm (or even the entire first ML algorithm) have been provided to the shared repository, this enables the second training of a second ML algorithm based on the synthetic imaging data that can then be generated by the first ML algorithm. I.e., inference of synthetic training medical imaging data can be implemented using the first ML algorithm. Respective details of such application of the first ML algorithm are explained next in connection with FIG. 5.

FIG. 5 is a flowchart of a method according to various examples. The method of FIG. 5 pertains to inference of synthetic training medical imaging data using a first ML algorithm. The synthetic training medical imaging data can depict an anatomical target region of at least one patient. The first ML algorithm can be trained using the method of FIG. 4.

The method of FIG. 5 can be executed by at least one processor upon loading program code. For instance, the method of FIG. 5 could be executed by the processor 61 of the device 6 the, upon loading program code from the memory 62.

Optional boxes are labeled with dashed lines in FIG. 5. At box 3105, the first ML algorithm is loaded from a shared repository (cf. FIG. 3: shared repository 89).

At box 3110, at least one latent space representation of the anatomical target region of at least one patient is established.

There are various options. For example, the latent space—i.e., the set of allowable latent space representations, could be learned during the training of box 3015. Then it would be possible to determine the at least one latent space representation to lie within the latent space. For instance, a latent space can be randomly sampled or sampled based on a predefined scheme.

Then, the first ML algorithm can be applied to the at least one latent space representation—i.e., the respective feature vector, sometimes also referred to as instance vector z—that has been established at box 3110, to thereby generate synthetic training medical imaging data at box 3115. The synthetic imaging data enables training a second ML algorithm.

Accordingly, at box 3120, it is optionally possible to train the second ML algorithm. The second machine-learning algorithm can be generally configured to process medical imaging data. Accordingly, the second machine-learning algorithm can be labeled medical imaging ML algorithm. Various tasks can be implemented by the second machine-learning algorithm, e.g., image segmentation, denoising, up sampling, reconstruction, etc.

At box 3125, it would then be optionally possible to provide the second ML algorithm, or at least parameter values thereof, to an imaging facility. For instance, referring to FIG. 3, it would be possible to provide parameter values of the second ML algorithm to the device 80. Then, the image processing tasks can be implemented on-site. As will be appreciated, domain-specific training is facilitated by the combined methods of FIG. 4 and FIG. 5. Nonetheless, the imaging data remains on-site, which saves bandwidth and protects privacy.

FIG. 6 is a schematic illustration of a workflow for training the medical-imaging ML algorithm 202. The workflow is generally structured into two phases 501, 502. Workflow steps of the phase 501 are executed on-site with an imaging facility; thus, they can implement the method of FIG. 4. Workflow steps of the phase 502 are executed off-site, e.g., at a central/shared server; thus, they can implement the method of FIG. 5.

At 511, new medical imaging data is acquired. For example, a cardiac CT scan could be performed.

At 512, an image quality control can be applied to the respective medical imaging data that has been acquired at 511. This can be implemented by a filtering according to box 3010 of FIG. 4. For instance, it could be checked whether the correct anatomy and view are present in the acquired medical imaging data. A check could be made to exclude calibration/phantom depiction.

Depending on whether a certain quality score exceeds a predefined threshold or not, it would be possible to selectively discard the previously acquired instance of the medical imaging data.

It is then possible, at 513, to add the respective instance of the imaging data to a mini-batch buffer.

511-513 can then be executed multiple times, until the mini-batch buffer has been populated with multiple instances of imaging data.

At 514, it is possible to perform a training of the image-synthesis ML algorithm 201. 514 accordingly implements box 3015.

At 515, upon completion of the training of the image-synthesis ML algorithm, at least the parameter values of the image-synthesis ML algorithm 201 are provided to a shared repository 89. The image-synthesis ML algorithm 201 can then be loaded, at 521, and used to generate synthetic training imaging data at 522. More specifically, the image-synthesis ML algorithm can be applied to at least one latent space representation—i.e., a feature vector sampling the latent space—of an anatomical target region to thereby generate the synthetic training medical imaging data that enables training the medical-imaging ML algorithm 202. The medical-imaging ML algorithm 202 is trained at 523.

As will be appreciated, the trained ML algorithm 201 is thus used off-line to generate the synthetic imaging data 211, e.g., with the patient distribution an image appearance/texture consistent with the clinical state. Segmented anatomies from any patient or synthetically generated masks can be used as an input to the image-synthesis ML algorithm to obtain a synthetic imaging data. This means that the medical-imaging ML algorithm can be fine-tuned/re-trained on the synthetic imaging data before deployment to a respective site.

Summarizing, techniques have been described that facilitate generating realistic synthetic training medical image data with a desire distribution of features. At the same time, acquired, real medical imaging data can be retained at the imaging facility of the hospital. Patient data can remain anonymous. The neural network used for generating the synthetic training medical image data can be trained on-site or even directly at the imaging facility such as an MRI scanner. Medical-imaging MR algorithms—e.g., for segmentation tasks, classification tasks, etc.—can be retrained/fine-tuned to a specific patient distribution and image appearance of an imaging facility, before deployment.

Although the invention has been shown and described with respect to certain preferred embodiments, equivalents and modifications will occur to others skilled in the art upon the reading and understanding of the specification. The present invention includes all such equivalents and modifications and is limited only by the scope of the appended claims.

For illustration, above, various scenarios have been described in which synthetic training medical imaging data is generated and a central server or, more generally, off-site with respect to an imaging facility. It would also be possible to use the trained machine-learning algorithm on-site at a imaging facility to generate the synthetic training medical imaging data.

The invention claimed is:

1. A computer-implemented method of performing a first training of a first machine learning algorithm for generating synthetic imaging data of an anatomical target region of at least one patient, the method comprising:
   obtaining multiple instances of imaging data of the anatomical target region of the at least one patient, the multiple instances of the imaging data being acquired at an imaging facility and being representative of a specific patient distribution and an image appearance of imaging data acquired at the imaging facility;
   on-site at the imaging facility and based on the multiple instances of the imaging data: performing the first training of the first machine learning algorithm for generating the synthetic imaging data; and
   upon completion of the first training: providing at least parameter values of the first machine learning algorithm but not the imaging data to a shared repository to thereby enable a domain specific training of a second machine learning algorithm based on further synthetic domain specific imaging data generated by the first machine learning algorithm using the domain specific parameter values, whereby the second machine learning algorithm is tuned to the specific patient distribution and image appearance of imaging data for the imaging facility before deployment by being trained on the synthetic domain specific imaging data.

2. The computer-implemented method of claim 1, wherein said performing of the first training comprises:
   generating at least one latent space representation using an encoder network for each one of the multiple instances of the imaging data;
   processing the latent space representations of the multiple instances of the imaging data by the first machine learning algorithm, to thereby obtain the synthetic imaging data; and
   updating parameter values of the first machine learning algorithm based on a comparison between the imaging data and corresponding synthetic imaging data.

3. The method of claim 1, wherein an input of the first machine learning algorithm comprises a segmentation map of the anatomical target region representing anatomical characteristics associated with the anatomical target region of the at least one patient.

4. The method of claim 1, further comprising:
   performing the domain specific training of the second machine learning algorithm, upon completing of the domain specific training: providing the second machine learning algorithm to at least one of the imaging facility or one or more further imaging facilities.

5. The method of claim 1, wherein the domain specific training comprises sampling latent space representations associated with the anatomical target region used as an input to the first machine learning algorithm.

6. The method of claim 1, further comprising:
   filtering the multiple instances of the imaging data based on their quality, such that the imaging data with the quality greater than a predefined threshold are used to perform the first training of the first machine learning algorithm.

7. The method of claim 2, further comprising:
providing the at least one latent space representation to the shared repository; and/or discarding the multiple instances of the imaging data.

8. The method of claim 2, wherein the first machine learning algorithm comprises a decoder to decode the at least one latent space representation to generate the synthetic imaging data.

9. The method of claim 1, further comprising:
pre-training the first machine learning algorithm based on offline imaging data associated with the anatomical target region of further patients.

10. A computer-implemented method for generating domain specific synthetic imaging data of an anatomical target region, the method comprising:
establishing at least one latent space representation associated with the anatomical target region of at least one patient from image data acquired at an imaging facility;
applying a trained first machine learning algorithm to the at least one latent space representation; and
generating, by the trained first machine learning algorithm, the domain specific synthetic imaging data to enable a second training of a second machine learning algorithm based on the domain specific synthetic imaging data, wherein the second machine learning algorithm is tuned to the anatomical target region and a specific patient distribution and an image appearance of imaging data for the imaging facility before deployment.

11. The method of claim 10, wherein the at least one latent space representation is established based on a segmentation map of the anatomical target region.

12. The method of claim 10, further comprising:
performing the second training of the second machine learning algorithm, upon completing of the second training: providing the second machine learning algorithm to a device on-site of the imaging facility.

13. The method of claim 10, wherein the second training comprises sampling a latent space of at least one latent space representation associated with the anatomical target region used as an input to the trained first machine learning algorithm.

14. A system for performing a first training of a first machine learning algorithm for generating domain specific synthetic imaging data of an anatomical target region of at least one patient, the system comprising:
at least one processor and a memory, the at least one processor being configured to load program code from the memory and to execute the program code, the at least one processor being configured, upon executing the program code, to:

obtain multiple instances of domain specific imaging data of the anatomical target region of the at least one patient, the multiple instances of the domain specific imaging data being acquired at an imaging facility, the multiple instances of the domain specific imaging data representative of a specific patient distribution and an image appearance of imaging data acquired at the imaging facility;

on-site at the imaging facility and based on the multiple instances of the domain specific imaging data: perform the first training of the first machine learning algorithm for generating the domain specific synthetic imaging data that is specific to a specific patient distribution and an image appearance of imaging data acquired at the imaging facility; and upon completion of the first training: provide at least parameter values of the first machine learning algorithm to a shared repository but not the imaging data, to thereby enable a second training of a second machine learning algorithm to fine tune the second machine learning algorithm to the specific patient distribution and image appearance of imaging data for the imaging facility based on further synthetic imaging data generated by the first machine learning algorithm using the parameter values.

15. A system for generating synthetic imaging data of an anatomical target region, the system comprising:
at least one processor and a memory, the at least one processor being configured to load program code from the memory and to execute the program code, the at least one processor being configured, upon executing the program code, to:

establish at least one latent space representation associated with the anatomical target region of at least one patient from a plurality of imaging data from an imaging facility, wherein the at least one latent space representation is specific to a specific patient distribution and an image appearance of imaging data acquired at the imaging facility;

apply a trained first machine learning algorithm to the at least one latent space representation; and generate, by the trained first machine learning algorithm, the synthetic imaging data to enable a second training of a second machine learning algorithm based on the synthetic imaging data wherein the second machine learning algorithm is tuned to the anatomical target region of the at least one patient before deployment.

* * * * *